(12) United States Patent
Herbert

(10) Patent No.: US 7,803,527 B2
(45) Date of Patent: Sep. 28, 2010

(54) INACTIVATED BOVINE HERPES VIRUS-1 AND METHODS

(75) Inventor: John Mateland Herbert, Larchwood, IA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/262,460

(22) Filed: Oct. 31, 2008

(65) Prior Publication Data

US 2009/0110697 A1 Apr. 30, 2009

Related U.S. Application Data

(60) Provisional application No. 61/001,208, filed on Oct. 31, 2007, provisional application No. 61/033,934, filed on Mar. 5, 2008.

(51) Int. Cl.
*C12Q 1/70* (2006.01)
(52) U.S. Cl. .......................................... 435/5; 424/229.1
(58) Field of Classification Search ........................ None
See application file for complete search history.

(56) References Cited

U.S. PATENT DOCUMENTS

2004/0081666 A1* 4/2004 Dominowski ............ 424/202.1

OTHER PUBLICATIONS

Bürki F, et al., "Viraemia and abortions are not prevented by two commerical Equine Herpesvirus-1 vaccines after experimental challenge of horses," *Vet Q.*, (Apr. 1990), vol. 12, No. 2, pp. 80-86.
Cravens R. L., et al., "Efficacy of a temperature-sensitive modified-live bovine herpesvirus type-1 vaccine against abortion and stillbirth in pregnant heifers," *J Am Vet Med Assoc.* (Jun. 15, 1996) vol. 208, No. 12, pp. 2031-2034.
Cortese Victor S., "Vaccinations to Optimize Reproductive Efficiency," *Kansas Vet Quarterly* (Jul.-Sep. 2000), vol. 3, No. 3,pp. 1-2,7.

Ficken M.D., et al., Evaluation of the Efficacy of a Modified-Live Combination Vaccine against Abortion Caused by Virulent Bovine Herpesvirus Type 1 in a One-Year Duration-of-Immunity Study*, *Vet Therapeutics*, (2006), vol. 7, No. 3, pp. 275-282.
Kahrs Robert F., "Infectious Bovine Rhinotracheitis," *Viral disease of cattle*. Ames, Iowa: Iowa State University Press, (1981), pp. 135-136.
Annual Report, Animal Disease Research and Diagnostic Laboratory Reports. Brookings, SD: South Dakota State University, 2005-2006).
McFeely R.A., et al., "Abortion in a dairy herd vaccinated for infectious bovine rhinotracheitis," *J Am Vet Med Assoc.*, (Sep. 15, 1968), vol. 153, pp. 657-661.
Nietfeld J., et al., "Multiple Abortions in a herd of cows vaccinated while pregnant with modified-live infectious bovine rhinotracheitis virus vaccine," American Association of Veterinary Laboratory Diagnosticians 43$^{rd}$ Annual Meeting, Abstracts, Oct. 21-23, 2000, vol. 14.
Pospisil Z, et al., "The efficacy of an inactivated IBR vaccine in the prevention of intra-uterine infection and its use in a disease-control programme," *Zentralbl Veterinarmed* [B], (1996), vol. 43, pp. 15-21.
Pospisil Z, et al., "Development of a disease control programme based on the use of an inactivated vaccine against infectious bovine rhinotracheitis," *Vet Microbiology* (1996), vol. 53, pp. 199-206.
Saunders J.R., et al., "Efficacy of an intramuscular infectious bovine rhinotracheitis vaccine against abortion due to the virus," *Can Vet J.*, (1972), vol. 13, pp. 273-278.
Smith M.W., et al., "Efficacy of an intranasal infectious bovine rhinotracheitis vaccine for the prevention of abortion in cattle," *Can Vet J.*, (1978), vol. 19, pp. 63-71.
Zimmerman Alicia D., et al., "Efficacy of bovine herpesvirus-1 inactivated vaccine against abortion and stillbirth in pregnant heifers," *J Am Vet Med Assoc.*, (Nov. 1, 2007), vol. 231, No. 9, pp. 1386-1389.
Wyler R, et al., "Infectious bovine rhinotracheitis/vulvovaginitis (BHV-1)" In: Wittman G, ed. *Herpes virus disease of cattle, horses and pigs. Developments in veterinary virology*. Boston, Kluwer Academic Publishers, (1989), pp. 1-72.

* cited by examiner

*Primary Examiner*—Ali R. Salimi

(57) ABSTRACT

This invention related to a method of immunizing cattle to reduce the effects of infection by bovine herpes virus 1, including abortion and stillbirth, by administering inactivated bovine herpes virus 1 prior to breeding.

20 Claims, 1 Drawing Sheet

# INACTIVATED BOVINE HERPES VIRUS-1 AND METHODS

BACKGROUND OF THE INVENTION

Infectious bovine rhinotracheitis is a clinically and economically important disease of cattle and is endemic in cattle populations throughout the world. Infectious bovine rhinotracheitis caused by BHV-1 is associated with a variety of clinical signs and can cause respiratory as well as reproductive disease. Bovine herpes virus type 1 is often associated with the bovine respiratory disease complex and can also predispose animals to secondary bacterial infections. Bovine herpes virus type 1 is spread through nasal secretions, droplets, genital secretions, serum, and fetal fluids. (Wyler R, Engels M, Schwyzer M. Infectious bovine rhinotracheitis/vulvovaginitis (BHV-1); In: Wittman G, ed. *Herpes virus disease of cattle, horses and pigs. Developments in veterinary virology*. Boston: Kluwer Academic Publishers, 1989; 1-72).

Nonvaccinated pregnant cattle are susceptible to the reproductive effects of BHV-1, and infections can result in abortion rates as high as 25%. These infections can also result in late-term abortions that can occur up to 100 days after infection. (Kahrs R F. *Viral disease of cattle*. Ames, Iowa: Iowa State University Press, 1981; 135-136.) Vaccination with either an MLV or inactivated vaccine is the most effective way to control the spread of BHV-1. Modified-live virus BHV-1 vaccines are administered parenterally (SC or IM) or IN, whereas inactivated vaccines are administered SC or IM. However, there have been adverse effects associated with MLV BHV-1 vaccines, including abortion in pregnant animals with unknown or questionable vaccine status (McFeely R A, Merritt A M, Stearly E L., Abortion in a dairy herd vaccinated for infectious bovine rhinotracheitis, *J Am Vet Med Assoc* 1968; 153:657-661; Nietfeld J C, et al., Multiple abortions in a herd of cows vaccinated while pregnant with modified-live infectious bovine rhinotracheitis virus vaccine, in *Proceedings. 43rd Annu Meet Am Assoc Vet Lab Diagn* 2000; 14; Annual Report, Animal Disease Research and Diagnostic Laboratory Reports. Brookings, S D: South Dakota State University, 2005-2006).

Five BHV-1 reproduction protection studies have been reported in the literature. Four of those studies have tested MLV vaccine efficacy (Saunders J R, Olson S M, Radostits O M., Efficacy of an intramuscular infectious bovine rhinotracheitis vaccine against abortion due to the virus, *Can Vet J* 1972; 13:273-278; Smith M W, Miller R B, Svoboda I, et al., Efficacy of an intranasal infectious bovine rhinotracheitis vaccine for the prevention of abortion in cattle, *Can Vet J* 1978; 19:63-71; Cravens R L, Ellsworth M A, Sorensen C D, et al., Efficacy of a temperature-sensitive modified-live bovine Herpes virus type-1 vaccine against abortion and stillbirth in pregnant heifers, *J Am Vet Med Assoc* 1996; 208: 2031-2034; Ficken M D, Ellsworth M A, Tucker C M., Evaluation of the efficacy of a modified-live combination vaccine against abortion caused by virulent bovine Herpes virus type 1 in a one-year duration-of-immunity study, *Vet Ther* 2006; 7:275-282). Only 1 study with an inactivated vaccine has been reported (Pospisil Z, et al., The efficacy of an inactivated IBR vaccine in the prevention of intra-uterine infection and its use in a disease-control programme. *Zentralbl Veterinarmed [B]* 1996; 43:15-21; Pospisil Z, et al., Development of a disease control programme based on the use of an inactivated vaccine against infectious bovine rhinotracheitis, *Vet Microbiol* 1996; 53: 199-206). This study, however, did not examine the effects of vaccination prior to breeding.

Accordingly, additional methods and compositions for controlling the effects of BHV-1 in cattle are desirable. In particular, effective methods and compositions involving an inactivated vaccine are desirable.

SUMMARY OF THE INVENTION

The present invention provides an inactivated BHV-1 vaccine and related method of administering the vaccine prior to breeding as a prophylactic treatment against abortion and/or stillbirth caused by BHV-1.

Accordingly, in one aspect, the invention relates to a method of immunizing cattle to reduce the effects of infection by bovine herpes virus 1, including abortion and stillbirth, by administering a composition comprising inactivated bovine herpes virus 1 prior to breeding.

In some embodiments, the composition is administered subcutaneously or intramuscularly.

In some embodiments, the composition is administered to the cattle up to about six months prior to breeding. The composition also can be administered to the cattle from about one to about three months prior to breeding. In some embodiments, the composition is administered to the cattle about two months prior to breeding.

In some embodiments, the composition is administered to the cattle two times before breeding. The second administration of the composition can be approximately 30 days after the first administration.

In some embodiments, the composition is administered to cattle prior to their first breeding season. The composition can be administered to the cattle two times prior to their first breeding season, and the second administration can occur up to about six months after the first administration. In some embodiments, the cattle receive a subsequent administration of the composition yearly after the initial administration, subsequent to their first breeding season.

In some embodiments, the composition includes one or more antigens derived from pathogens selected from the group consisting of *Vibrio* and *Leptospires*.

In some embodiments, the composition further comprises one or more antigens derived from bovine virus diarrhea type 1, bovine virus diarrhea type 2, parainfluenza Type 3, or bovine respiratory syncytial virus. In some embodiments, the composition comprises antigens from each of these viruses. In some embodiments, the composition additionally comprises one or more antigens from pathogens *Vibrio* and *Leptospires*. In some embodiments, the composition comprises one or more antigens derived from a *Hardjo bovis* isolate of *Leptospires*.

In some embodiments, the composition comprises an adjuvant. The adjuvant can be an oil-based emulsion.

BRIEF DESCRIPTION OF THE DRAWINGS

In accordance with particular embodiments of the invention.

DETAILED DESCRIPTION OF THE INVENTION AND EMBODIMENTS

Figure 1:
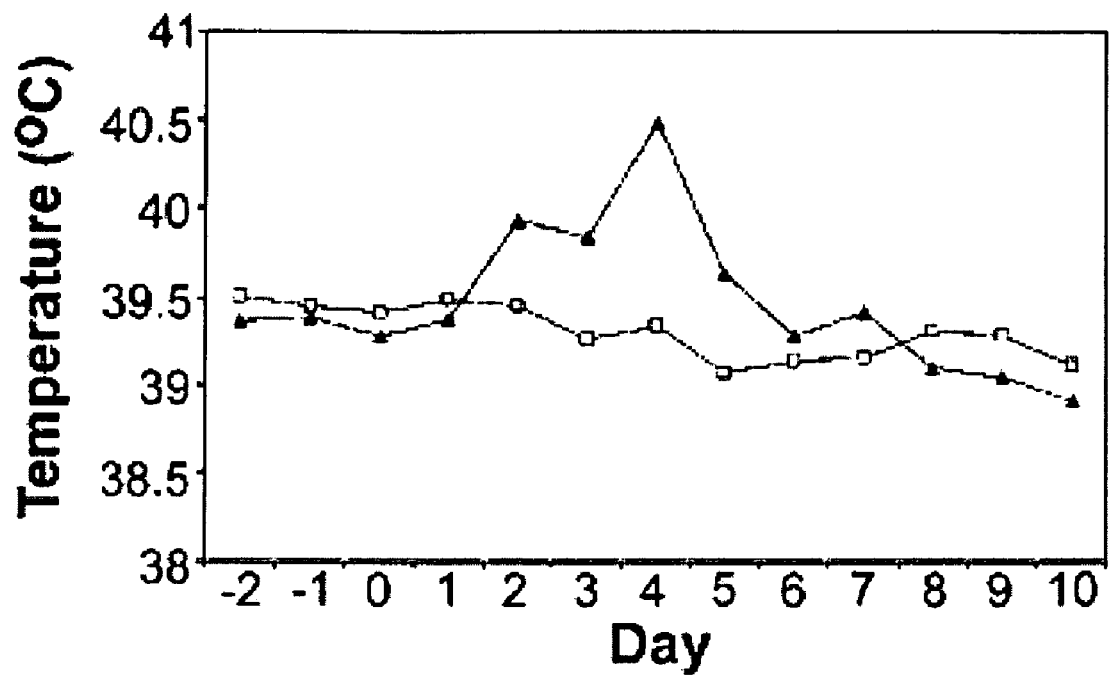
FIG. 1 is a graphic representation of mean rectal temperatures after challenge with BHV-1 in control heifers (triangles) and heifers vaccinated with an inactivated vaccine (squares), measured 2 days prior to challenge (day-2) until 10 days after challenge. Difference between groups was significant (P<0.05) on days 2, 3, 4, 5, and 7.

The following definitions are meant to clarify, but not limit, the terms defined. If a particular term used herein is not specifically defined, such term should not be considered indefinite. Rather, terms are used within their accepted meanings.

As used herein, the phrase "inactivated," e.g, as in "inactivated virus" or "inactivated bovine Herpes virus 1" refers to virus rendered incapable of replication or incapable of causing an infection.

As used herein, the term "administering" includes any method of contacting an animal with a composition in a manner that can lead to an immune response to the composition. "Administering" includes, but is not limited to, subcutaneous, intramuscular, and intranasal administration.

As used herein, the term "booster" refers to a second or any subsequent administration of a previously administered composition.

As used herein, the term "breeding" includes all forms of fertilization of an animal, including artificial insemination, in vitro fertilization, and natural breeding.

Abbreviations include: "IBR"—Infectious Bovine Rhinotracheitis; "BHV-1"—Bovine herpes virus type 1; "MLV"—Modified-Live Virus; "IN"—IntraNasal; "SC"—SubCutaneous; "IM"—IntraMuscular; "BVDV"—Bovine Viral Diarrhea Virus.

The present inventors have demonstrated that vaccination of cattle prior to breeding using an inactivated BHV-1 can provide protection against the effects the virus, including a reduction in abortion and stillbirth. The method of the invention provides these benefits without risking the abortifacient effects of administering a modified live virus vaccine.

Of the heifers that received vaccine according to the method of the present invention, 18 of 21 (85.7%) were protected from abortion following challenge, whereas all 14 control heifers aborted. These results indicate that an inactivated BHV-1 vaccine can protect against abortion resulting from a substantial challenge infection, with efficacy similar to that of modified-live BHV-1 vaccines (see *J Am Vet Med Assoc.* 2007 Nov. 1; 231(9):1386-9) while avoiding some risks associated with such vaccines.

Although some studies have suggested that inactivated herpes virus-1 vaccines are not effective in protecting against abortion and stillbirth when administered prior to breeding (Bürki F, et al., *Vet Q.* 1990 April; 12(2):80-6), the present inventors have obtained results indicating that an inactivated multivalent vaccine containing BHV-1 administered before breeding protected against abortion despite a virulent BHV-1 challenge at approximately 180 days of gestation. Vaccinated heifers had fewer clinical signs, lower rectal temperatures, and significantly fewer abortions. Among vaccinated heifers, 85.7% were protected against abortion, whereas all control heifers (14/14) aborted following challenge. Bovine herpes virus type 1 was isolated from all aborted fetuses, and no other pathogens were detected. Additionally, positive identification of heifer-fetus pairs was accomplished via DNA parentage testing.

The ability of an inactivated vaccine to protect heifers from abortion also can be important because inactivated vaccines can be administered during gestation and lactation. Some MLV vaccines are presently approved for administration during gestation and lactation; however, abortions can occur when these vaccines are administered to animals with unknown or questionable vaccine status. (McFeely R A, et al., *J Am Vet Med Assoc* 1968; 153:657-661; Nietfeld J C, et al., Multiple abortions in a herd of cows vaccinated while pregnant with modified-live infectious bovine rhinotracheitis virus vaccine, in *Proceedings, 43rd Annu Meet Am Assoc Vet Lab Diagn* 2000; 14; Annual Report, Animal Disease Research and Diagnostic Laboratory Reports. Brookings, S D: South Dakota State University, 2005-2006).

As noted above, several BHV-1 reproduction protection studies that used MLV vaccines can be found in the literature. (*Can Vet J* 1972; 13:273-278; *Can Vet J* 1978; 19:63-71; *J Am Vet Med Assoc* 1996; 208:2031-2034; *Vet Ther* 2006; 7:275-282.) Further, a single study on inactivated vaccines has been published (*Zentralbl Veterinarmed [B]* 1996; 43:15-21; *Vet Microbiol* 1996; 53: 199-206). However, challenge models and study designs are not consistent among studies, making it difficult to compare results from those studies with results of the present study. Three studies used MLV vaccine administered IM prior to breeding, followed by either an IN challenge (*Can Vet J* 1972; 13:273-278) or an IV challenge (*J Am Vet Med Assoc* 1996; 208:2031-2034; *Vet Ther* 2006; 7:275-282). One study used an IN administered vaccine prior to breeding, followed by an IN challenge (*Can Vet J* 1978; 19:63-71). Only 1 study that used an inactivated vaccine has been reported in the literature (*Zentralbl Veterinarmed [B]* 1996; 43:15-21; *Vet Microbiol* 1996; 53: 199-206). That study involved vaccinating bred cattle from seropositive or seronegative herds and used either an intratracheal or IV challenge.

In the study reported by Saunders et al., (*Can Vet J* 1972; 13:273-278) heifers were vaccinated IM once or twice with an MLV and challenged IN at either 3, 4, 5, or 6 months of gestation. After challenge, 10 of 16 control heifers and 1 of 17 vaccinates aborted. However, BHV-1 was isolated from only 3 fetal placentas and 1 fetal tissue sample. In the study by Smith et al., heifers were vaccinated once IN with an MLV vaccine and challenged IN at 7.5 to 9 months of gestation (Can Vet J 1978; 19:63-71). Twelve of 16 control heifers had fetal loss following challenge, and BHV-1 was isolated from 11 of the 12 fetuses. In contrast, in the study reported here, all control heifers aborted.

Additional studies of MLV vaccines have used a challenge model and a study design comparable to used by the present inventors in evaluating the present invention. In a prior BHV-1 study, an MLV vaccine was administered IM 2 times before breeding and heifers were challenged at approximately 6 months of gestation (*J Am Vet Med Assoc* 1996; 208:2031-2034). Nine of 10 vaccinated heifers were protected from BHV-1-induced abortion, whereas all 10 control heifers had fetal loss (8 abortions and 2 stillbirths). Interestingly, no BHV-1 was isolated from any of the aborted or stillborn fetuses, although histologic findings and results of BHV-1 fluorescent antibody testing were indicative of BHV-1 infection.

In a study supporting one aspect of the invention, BHV-1 was isolated from all fetuses. In the MLV study reported by Fickens et al., heifers were vaccinated once prior to breeding and challenged IV at 6 to 7 months of gestation. In the vaccinated group, 84.2% were protected against abortion, whereas 100% of control heifers had fetal loss. Bovine herpes virus type 1 fetal infection was confirmed via histologic examination, virus isolation, or both (Ficken M D, et al., *Vet Ther* 2006; 7:275-282). Thus, results of those MLV studies discussed above were comparable to results of the present inventor's study. In addition, the same challenge strain and model were used; however, the present invention and all investigative work utilized an inactivated vaccine.

Results of the only published BHV-1 fetal loss study that used an inactivated BHV-1 vaccine are difficult to compare with those of the present invention because of differences in study design (*Zentralbl Veterinarmed [B]* 1996; 43:15-21; *Vet Microbiol* 1996; 53: 199-206). In the BHV-1 fetal loss study, seropositive and seronegative pregnant cattle were vaccinated SC between 5 and 6 months of gestation. Cattle were challenged intratracheally or IV at approximately 7 months of gestation. Twenty-one days following challenge, the fetuses from 3 vaccinated cows (2 challenged intratracheally and 1 challenged IV) and fetuses from 2 control cows (1 challenged intratracheally and 1 challenged IV) were obtained by Caesarian section and tested for BHV-1. Fetuses removed from the 2 intratracheally challenged vaccinated cows yielded negative results for BHV-1, whereas the fetus from the IV challenged vaccinated cow yielded positive results. Both of the control fetuses yielded positive results for BHV-1. This indicates the importance of the route of challenge for evaluating BHV-1-induced fetal loss. All remaining vaccinated cattle (27/27) had normal full term calves, whereas 4 of 8 control cattle had BHV-1 fetal loss as confirmed via virus isolation.

The studies supporting the present invention differed in that heifers were vaccinated prior to breeding; however, they were challenged at approximately 6 months of gestation, indicating vaccine duration of at least 230 days, compared with just 21 days in the previous study. In addition, the inventors' study used only the IV challenge method, and vaccination protected 85.7% of the fetuses in the vaccinated group, whereas the other study had only 1 vaccinated animal challenged IV and that animal aborted.

Below, Table 1 shows comparative results from three modified-live vaccine preparations relative to the vaccine preparation in one embodiment of the present invention.

TABLE 1

| | Abortions | | | |
|---|---|---|---|---|
| Product | Type | V | C | % Protection |
| Bovishield ® GOLD 5 FP + VL5 | MLV | 3/19 | 10/10 | 84 |
| Cattlemaster ® GOLD FP + VL5 | MLV | 1/13 | 11/12 | 92 |
| Vista ® 5 SQ | MLV | 6/16 | 14/14 | 63 |
| Vira Shield ® 6 | Kv | 3/21 | 14/14 | 86 |

Results of the present study provided evidence that an inactivated BHV-1 vaccine can provide excellent protection against fetal loss from BHV-1 infections. This is compelling evidence against the common misconception that only MLV vaccines can provide protection against BHV-1. (Cortese V S., *Kansas Vet Q* 2000; 3:1-2, 7) The protection generated by an inactivated BHV-1 vaccine according to the present invention can be provided without any danger of the possible abortifacient properties of the MLV BHV-1 vaccines.

EXAMPLES

Example 1

Vaccination of Heifers, Breeding, and Inoculation

To evaluate the efficacy of an inactivated bovine Herpes virus-1 (BHV-1) vaccine to protect against BHV-1 challenge-induced abortion and stillbirth, heifers were vaccinated before breeding with a commercially available BHV-1 inactivated vaccine SC or IM. The estrus cycle was then synchronized, and heifers were artificially inseminated 30 to 60 days after vaccination. Heifers (n=21) were challenge inoculated IV at approximately 180 days of gestation with virulent BHV-1. Fourteen control heifers were not vaccinated. Clinical signs of BHV-1 infection were monitored for 10 days following challenge; serologic status and occurrence of abortion or stillbirth were evaluated until time of calving.

Animals

Fifty-two 6-9 month old beef heifers (Angus cross) were assigned to three groups (group 1, IM vaccinates; group 2, SC vaccinates; and group 3 sham-vaccinated controls. All heifers were tested for the presence of BHV-1 and BVDV antibodies by serum neutralization prior to each vaccination and prior to challenge. Thirty-two heifers were vaccinated with the Virashield 6, a commercial inactivated combination vaccine: 16 heifers were vaccinated IM (treatment group 1); 16 heifers were vaccinated SC (treatment group 2). Twenty heifers were sham vaccinated with an oil adjuvanted vaccine that did not contain any viral antigens (treatment group 3). All heifers were booster vaccinated 29 days later. Heifers were synchronized and artificially inseminated ~50 days following booster vaccination (see details below).

After confirmation of pregnancy, thirty-five 6- to 9-month-old beef (Angus cross) heifers in treatment group 1 (n=12) were designated as IM vaccinates, heifers in treatment group 2 (n=9) were designated as SC vaccinates, and heifers in treatment group 3 (n=14) were designated as control heifers. Heifers were managed according to routine animal husbandry procedures and were isolated from any other cattle.

Prevaccination Serological Assays

Blood was collected from all heifers prior to vaccination. All heifers were seronegative for antibodies against BHV-1 and BVDV and were negative to BVDV via ear notch testing. Serum samples were tested for BHV-1 and BVDV serum neutralizing antibody titers by use of the constant virus decreasing serum assay. Two-fold serial dilutions (range, 1:2 to 1:1,024) of sera in quadruplicate were incubated with a constant viral titer (<500 $TCID_{50}$) before inoculation of Madin-Darby bovine kidney cells in microtiter tissue culture plates. Plates were incubated at 37° C. with 5% $CO_2$ for 4 to 6 days for BHV-1 and 5 to 7 days for BVDV before being evaluated for virus induced cytopathic effect. The reciprocal of the last dilution that prevented cytopathic effect was designated the serum neutralizing antibody titer. Geometric mean values were calculated by use of $log_2$ titers.

Vaccination

Thirty-five heifers were vaccinated at approximately 1 year of age (day 0). Twelve heifers in group 1 were vaccinated IM and 9 heifers in group 2 were vaccinated SC by use of a commercially available inactivated combination vaccine according to manufacturer's recommendations (VIRASHIELD 6, Novartis Animal Health, Larchwood, Iowa). VIRASHIELD 6 contains antigens derived from bovine Herpes virus 1, bovine virus diarrhea type 1, bovine virus diarrhea type 2, parainfluenza Type 3, and bovine respiratory syncytial virus. The remaining 14 control heifers in group 3 were sham vaccinated with an oil-adjuvanted vaccine that did not contain viral antigens. All heifers were booster vaccinated with the appropriate vaccine on day 29. Heifers were observed daily after each vaccination for vaccine-related adverse events.

Synchronization and Breeding

The heifers' estrus cycles were synchronized by use of a vaginal implant, (EAZI-BREED CIDR implants, Pharmacia & UpJohn Co, Kalamazoo, Mich.) a gonadotrophin-releasing hormone, and prostaglandin. Implants were inserted vaginally, and gonadorelin diacetate tetrahydrate (OVACYST, Phoenix Scientific Inc, St Joseph, Mo.) was administered IM. The implants were removed, detectors (KAMAR HEAT-MOUNT detectors, KAMAR Inc, Steamboat Springs, Colo.) were placed on the tail-head area to aid in estrus detection, and the heifers were administered dinoprost tromethamine (PROSTAMATE, Phoenix Scientific Inc, St Joseph, Mo.) IM. Heifers were observed twice daily for signs of estrus (color change in detector from white to red), and heifers with a red detector were artificially inseminated 12 hours later. At breeding, the estrus detector was removed. Two virgin BHV-1 vaccinated clean-up bulls were put in with the heifers for 3 weeks following artificial insemination. The bulls had been vaccinated with a commercially available inactivated viral vaccine (VIRASHIELD 5, Novartis Animal Health, Larchwood, Iowa) at 2, 5, and 7 months of age and were revaccinated at 11 months of age with the same product used on the heifers (VIRASHIELD 6). The bulls were purchased at 15 months of age and held in separate facilities for approximately 2 months prior to exposure to the heifers. Semen from both clean-up bulls yielded negative results for BVDV and BHV-1 by use of a PCR assay and negative results for BVDV by use of ear notch testing with an ELISA. A semen sample from the bull used for artificial insemination also yielded negative results for BVDV by use of a PCR assay. Heifers were palpated transrectally prior to challenge to confirm pregnancy status.

Challenge Inoculation

All heifers received an IV challenge with 2 mL of BHV-1 (Cooper strain, National Veterinary Services Laboratory, Ames, Iowa, approx $3 \times 10^6$ $TCID_{50}$/mL) at approximately 180 days of gestation and 230 days after the second vaccination. Clinical observations were performed daily from 2 days prior to challenge through day 10 after challenge. Each heifer was visually examined in the pen prior to handling and scored for clinical signs, including abnormal respiration, nasal and ocular discharge, nasal lesions, cough, and attitude, by use of a scale of 0 to 3, with the absence of a clinical sign scored as 0 and the most severe clinical sign scored as 3. After visual assessment, heifers were restrained and rectal temperatures were determined. (GLA Agriculture Electronics, San Luis Obispo, Calif.). All heifers were observed daily for signs of abortion from the time of challenge through the time of calving.

Serologic Testing

Blood was collected via jugular venipuncture from the heifers prior to each vaccination, prior to challenge, 10 days following challenge, and 64 days following challenge. Serum neutralizing antibody titers against BHV-1 were determined by use of the constant virus decreasing serum assay. Blood was also collected via jugular venipuncture from neonatal calves of the vaccinated heifers prior to colostrum ingestion and tested for BHV-1 neutralizing antibody.

Fetal Tissue Collection and Testing

Samples were collected from aborted fetuses and tested for BHV-1 and BVDV. Prior to testing, fetal spleen samples were matched to the appropriate dam (via dam tail switch hair samples) by use of DNA parentage testing. (Veterinary Genetics Laboratory, University of California, Davis, Calif.) Heart blood, pleural fluid, or both were tested for neutralizing antibody titers against BHV-1 and BVDV. Lung, placenta, and stomach contents were tested for abortagenic bacteria, and a kidney sample was tested for leptospiral organisms via fluorescent antibody testing. (Animal Disease Research and Diagnostic Laboratory, South Dakota State University, Brookings, S. Dak.) Thymus, lung, liver, spleen, kidney, and brain were each tested for BHV-1 and BVDV via virus isolation. (Rural Technologies Inc, Brookings, S. Dak.) Briefly, dilutions of processed samples were made, and each diluted sample was added in triplicate for BHV-1 and in quadruplicate for BVDV to BVDV-free bovine turbinate cell monolayers in microtiter tissue culture plates. The BHV-1 culture plates were incubated for 2 to 3 days at 37° C. with 5% $CO_2$. For BVDV, the culture plates were incubated for 3 to 4 days at 37° C. with 5% $CO_2$, followed by 2 additional passages incubated for 3 to 4 days each. Results were considered positive if BHV-1 or BVDV virus-specific staining was observed in inoculated cells.

Statistical Analysis

The Fisher exact test was used to test the hypothesis of no difference in frequency of abortion or stillbirths between the 2 vaccinated groups (SC vs IM); the results indicated no significant differences, and therefore, the 2 vaccinate groups were combined for all further analyses. The proportion of animals that aborted was analyzed by use of the Fisher exact test. Temperatures were compared between the control and vaccinated groups by use of ANCOVA, and serum neutralization data were analyzed by use of ANCOVA and ANOVA. Clinical scores between the control and the vaccinated groups were evaluated by use of a parametric repeated measures ANCOVA. For all comparisons, $P<0.05$ was considered significant.

Results

Figure 2:
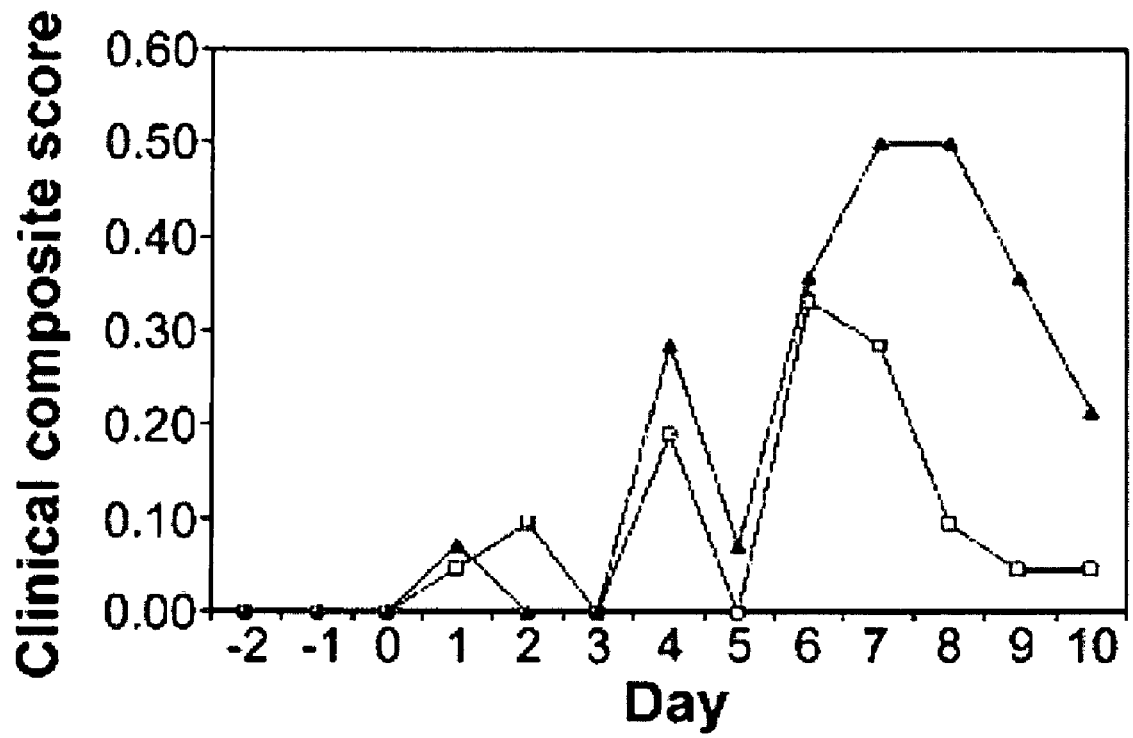
FIG. 2 is a graphic representation of mean composite clinical scores after challenge with BHV-1 in the same heifers as in FIG. 1. Difference between groups was significant (P<0.05) on days 7 through 10.

Adverse vaccine reactions were not observed in any heifers. Following challenge, body temperature was measured rectally in all heifers from 2 days prior to challenge to 10 days after challenge, with the mean determined for each group (FIG. 1). Control heifers had higher mean temperatures than vaccinates over the entire course of the trial. Significant ($P<0.001$) differences were detected on days 2 to 5 after challenge, with the mean temperature in the control group higher than 39.7° C. (103.5° F. [study cutoff value for pyrexia]) on days 2 (39.9° C. [103.8° F.]), 3 (39.8° C. [103.6° F.]), and 4 (40.4° C. [104.7° F.]). Clinical observation scores were totaled for each heifer beginning 2 days prior to challenge through 10 days after challenge, and the mean of these composite scores was determined for each group (FIG. 2). Control heifers (group 3) had significantly ($P=0.03$) higher mean clinical scores than vaccinates from 7 to 10 days after challenge. Mean clinical scores for group 1 peaked on days 4 and 6 after challenge; those in group 2 peaked on days 4, 6, and 7 after challenge.

Seventeen heifers aborted following challenge. Three of 21 (14.3%; 1 from the SC group and 2 from the IM group) heifers from the vaccinated group and 14 of 14 heifers in the control group aborted. The vaccinated group had significantly ($Ps \leq 0.001$) fewer abortions, compared with the control group.

TABLE 2

| Group | Treatment | Fetal Abortions | BHV-1 positive fetuses |
|---|---|---|---|
| 1 | Vaccinated IM | 2 of 12 (17%) | 2 of 2 (100%) |
| 2 | Vaccinated SC | 1 of 9 (11%) | 1 of 1 (100%) |
| 3 | Control | 14 of 14 (100%) | 14 of 14 (100%) |

All heifers had titers of 0 at the time of the first vaccination. Heifers in the vaccinated group had significantly ($P<0.001$) higher mean titers (2.71) than did control heifers (0.09; 1 heifer had a titer of 2.3) on the day of second vaccination. On the day of challenge, vaccinated heifers had a mean titer of 5.10, which was significantly (P<0.001) higher than that of control heifers, of which 2 had a mean titer of 0.16 (1 had a titer of 1.3 [the animal with a titer of 2.3 at the second vaccination], and 1 had a titer of 1.0). Vaccinated heifers had a mean titer of 6.58, and the control heifers had a mean titer of 3.81. On day 64 following challenge, vaccinated heifers had a mean titer of 6.47 and the control heifers had a mean titer of 6.38.

TABLE 3

| Group | Treatment | 0 DPV1 | 0 DPV2 | −1 DPC | 10 DPC | 64 DPC |
|---|---|---|---|---|---|---|
| 1 + 2 | IM + SC | 0.00 | 2.71 | 5.10 | 6.58 | 6.47 |
| 1 | IM | 0.00 | 2.33 | 5.02 | 6.58 | 6.54 |
| 2 | SC | 0.00 | 3.08 | 5.18 | 6.58 | 6.39 |
| 3 | Control | 0.00 | 0.09 | 0.16* | 3.81 | 6.38 |

Tissues from all aborted fetuses yielded positive results for BHV-1 via virus isolation and fluorescent antibody testing. The fetal tissues yielded negative results for BVDV via virus isolation, negative results for *Leptospira* spp via fluorescent antibody assay, and negative results for bacterial pathogens via culture.

All calves that had not suckled (n=16) yielded negative results for anti-BHV-1 antibodies. Two of the neonatal calves suckled prior to sample collection and were excluded from the serologic analysis.

Example 2

Inactivated Bovine Herpes Virus 1 Vaccine

According to one embodiment of the invention, an inactivated BHV-1 vaccine may be prepared as follows:

Briefly, bovine origin cultures are grown (37±2° C.) to confluency of >90% in EMEM (Earle's Minimal Essential Media [containing 5%-10% nutrient serum of bovine or equine origin]). Cell cultures are then inoculated with a Multiplicity of Infection (MOI) between 0.002-0.0002 using EMEM containing 0-2% nutrient serum. Cultures are allowed to incubate at 37±2° C. for 2-5 days until cytopathic effect (CPE) is ≧50%. Cultures may be harvest by mechanical agitation or by freeze-thaw method at −40° C. or colder. Harvested cultures should be equal to or exceed $1\times10^4$ Tissue Culture Infectious $Dose_{50}$/ml (TCID50/ml).

Beta-propiolactone (BPL) Stock Solution (>99% pure) is stored at −52° C. or lower. Cold concentrated BPL is added to the viral fluids at a concentration not to exceed 0.1% volume to volume. Alternatively, concentrated BPL may diluted (1:10) in cold, sterile, deionized $H_2O$ and added at a concentration not to exceed 1% volume to volume.

Fluids are mixed so that all surfaces of container are contacted by liquid. Viral fluids are placed at 35-39° C. and mixed for 18-48 hours. The pH of viral fluids are adjusted with nitric acid or NaOH to a biologically neutral pH following inactivation (pH 7.0±0.2). Fluids are then stored at 2-70° C. until further processing.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A method for immunizing cattle, the method comprising:

administering to the cattle, within about 6 months prior to breeding, a composition that includes inactivated bovine herpesvirus-1 (BHV-1) and an adjuvant, wherein the cattle that become pregnant and become exposed to BHV-1 subsequent to the administering, have a reduced rate of abortions or stillbirths as compared to cattle that have not been administered the composition and become exposed to BHV-1 during or immediately prior to pregnancy.

2. The method of claim 1, wherein the BHV-1 is inactivated using beta-propiolactone (BPL).

3. The method of claim 2, wherein the BPL is from about a 0.1% to a 1.0% solution of BPL.

4. The method of claim 3, wherein the BHV-1 is contacted with the solution of BPL at a temperature of about 35-39° C. for about 18-48 hours.

5. The method of claim 1, wherein the adjuvant is an oil-based emulsion.

6. The method of claim 1, wherein the administering within about 6 months prior to breeding occurs at about 1-3 months prior to the breeding.

7. The method of claim 1, wherein the administering within about 6 months prior to breeding occurs at about 30-60 days prior to the breeding.

8. The method of claim 1, wherein the administering of the composition to the cattle includes a first and a second administering, the second administering occurring within about 6 months prior to breeding the cattle, and the first administering occurring within about 6 months prior to the second administering.

9. The method of claim 1, wherein the administering is subcutaneous or intramuscular.

10. The method of claim 1, wherein the composition additionally includes one or more antigens from bovine virus diarrhea type 1 (BVD1), bovine virus diarrhea type 2 (BVD2), parainfluenza type 3 (PI3) and bovine respiratory syncytial virus (BRSV).

11. The method of claim 1, wherein the composition additionally includes antigens from one or more of *Vibrio* and *Leptospires*.

12. The method of claim 11, wherein the *Leptospires* is a *Hardjo bovis* isolate.

13. A method for protecting a bovine fetus against reproductive effects of BHV-1, the method comprising:

administering an oil-adjuvanted, inactivated BHV-1 vaccine composition to cows or heifers within 6 months prior to pregnancy, to increase serum titers of antibodies specific for BHV-1 and to provide protection against the reproductive effects of BHV-1 in cows or heifers that become pregnant, wherein protection against the reproductive effects of BHV-1 means that vaccinated cows or heifers have a lower rate of abortion or stillbirth of the fetus than do unvaccinated cows or heifers.

14. The method of claim 13, wherein the administering of the vaccine composition includes a first administration no more than 6 months prior to a second administration, the second administration occurring within 6 months prior to pregnancy.

15. The method of claim 14, wherein the serum titer of antibodies specific for BHV-1 in cattle administered the vaccine composition is greater at the time of the second administration than at the time of the first administration.

16. The method of claim 13, wherein the vaccine composition includes inactivated bovine virus diarrhea type 1

(BVD1), bovine virus diarrhea type 2 (BVD2), parainfluenza type 3 (PI3) and bovine respiratory syncytial virus (BRSV), and at least one antigen from *Vibrio* and from a *Leptospires Hardjo bovis* isolate.

17. A method for reducing, in cattle, rate of abortions associated with BHV-1, the method comprising:

providing to female cattle, prior to pregnancy, two administrations of a composition that includes inactivated BHV-1, BVD1, BVD2, PI3, BRSV, and an oil-based emulsion adjuvant, wherein the first administration occurs within one year of breeding the cattle and the second administration occurs within 6 months of breeding the cattle, and wherein cattle that become pregnant as a result of the breeding have a reduced rate of abortions associated with BHV-1 than do control cattle that have not been provided with the administrations of the composition.

18. The method of claim 17, wherein the reduced rate of abortions means pregnant cattle provided the administrations have statistically significant fewer abortions than control pregnant cattle not provided the administrations.

19. The method of claim 17, wherein the first administration occurs within 6 months of breeding the cattle and the second administration occurs within 3 months of breeding the cattle.

20. The method of claim 17, wherein the composition includes antigens from *Vibrio* and from a *Hardjo bovis* isolate of *Leptospires*.

* * * * *